US011124641B2

(12) United States Patent
DeMarco et al.

(10) Patent No.: US 11,124,641 B2
(45) Date of Patent: *Sep. 21, 2021

(54) THERMOPLASTIC INJECTION MOLDED AND FLUSHABLE MATERIAL

(71) Applicant: Kimberly-Clark Worldwide, Inc., Neenah, WI (US)

(72) Inventors: Alphonse DeMarco, Seal Harbour (CA); Gregory J. Wideman, Menasha, WI (US); Peter S. Lortscher, Neenah, WI (US); Austin N. Pickett, Menasha, WI (US); Mark M. Mleziva, Appleton, WI (US); Garry R. Woltman, Appleton, WI (US); Michael G. Shlepr, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 79 days.

This patent is subject to a terminal disclaimer.

(21) Appl. No.: 16/344,695

(22) PCT Filed: Nov. 17, 2017

(86) PCT No.: PCT/US2017/062196
§ 371 (c)(1),
(2) Date: Apr. 24, 2019

(87) PCT Pub. No.: WO2018/102154
PCT Pub. Date: Jun. 7, 2018

(65) Prior Publication Data
US 2020/0056032 A1    Feb. 20, 2020

Related U.S. Application Data

(60) Provisional application No. 62/428,288, filed on Nov. 30, 2016.

(51) Int. Cl.
*C08L 29/04* (2006.01)
*C08L 71/02* (2006.01)
(Continued)

(52) U.S. Cl.
CPC ............. *C08L 29/04* (2013.01); *A61F 13/266* (2013.01); *C08K 5/053* (2013.01); *C08L 23/00* (2013.01);
(Continued)

(58) Field of Classification Search
None
See application file for complete search history.

(56) References Cited

U.S. PATENT DOCUMENTS 5,002,526 A    3/1991 Herring
5,047,181 A    9/1991 Occhionero et al.
(Continued)

FOREIGN PATENT DOCUMENTS

CN    201769308 U    3/2011
CN    103691956 A    4/2014
(Continued)

OTHER PUBLICATIONS

US 8,759,427 B2, 06/2014, Bond et al. (withdrawn)

*Primary Examiner* — Richard A Huhn
(74) *Attorney, Agent, or Firm* — Kimberly-Clark Worldwide, Inc.

(57) ABSTRACT

A water-dispersible injection-moldable composition includes partially-hydrolyzed polyvinyl alcohol (PVOH), polyethylene glycol (PEG), plasticizer, and a hydrophobic polymeric component, wherein the composition has a melt flow index of 5-180. The hydrophobic polymeric component can be a colorant within an ethylene matrix or polyethylene. The composition is flushable according to Guidance Document for Assessing the Flushability of Nonwoven Consumer
(Continued)

Products (INDA and EDANA, 2006); Test FG 522.2 Tier 2—Slosh Box Disintegration Test. The PVOH has a hydrolysis of 87% to 89%.

12 Claims, 2 Drawing Sheets

(51) Int. Cl.
  *C08L 23/00*   (2006.01)
  *C08K 5/053*   (2006.01)
  *A61F 13/26*   (2006.01)
(52) U.S. Cl.
  CPC ........... C08L 71/02 (2013.01); C08L 2205/03 (2013.01); C08L 2205/06 (2013.01)

(56) References Cited

U.S. PATENT DOCUMENTS

| | | | |
|---|---|---|---|
| 5,582,788 A | 12/1996 | Collette et al. | |
| 5,661,217 A | 8/1997 | Honeycutt et al. | |
| 5,804,653 A | 9/1998 | Weng | |
| 5,897,410 A | 4/1999 | Ferraro | |
| 5,954,683 A * | 9/1999 | Downs .................... | A61F 13/26 604/15 |
| 6,730,057 B2 | 5/2004 | Zhao et al. | |
| 7,045,083 B2 | 5/2006 | Gardner | |
| 8,569,402 B2 | 10/2013 | Henderson et al. | |
| 2003/0036721 A1 | 2/2003 | Zhao et al. | |
| 2003/0040695 A1 | 2/2003 | Zhao et al. | |
| 2006/0025740 A1 | 2/2006 | Osborn et al. | |
| 2007/0276317 A1 | 11/2007 | Henderson et al. | |
| 2008/0167597 A1 * | 7/2008 | Dougherty .............. | C08L 53/00 604/12 |
| 2010/0016780 A1 | 1/2010 | VanDenBogart et al. | |
| 2012/0328804 A1 | 12/2012 | Allen et al. | |
| 2013/0004691 A1* | 1/2013 | Allen ..................... | C08L 77/06 428/36.92 |
| 2015/0148461 A1 | 5/2015 | Wang et al. | |
| 2015/0148732 A1 | 5/2015 | Wang et al. | |
| 2015/0148733 A1 | 5/2015 | Wang et al. | |
| 2016/0008671 A1 | 1/2016 | Bhargava et al. | |

FOREIGN PATENT DOCUMENTS

| | | |
|---|---|---|
| DE | 640448 C | 1/1937 |
| EP | 635545 A2 | 1/1995 |
| EP | 1368069 B1 | 12/2009 |
| FR | 1364117 A | 6/1964 |
| GB | 1259349 A | 1/1972 |
| GB | 1337446 A | 11/1973 |
| JP | 6049084 A2 | 2/1994 |
| JP | 2000072887 A | 3/2000 |
| JP | 2001039428 A | 2/2001 |
| JP | 2009161405 A | 7/2009 |
| KR | 100197036 B1 | 6/1999 |
| WO | 9604338 A1 | 2/1996 |
| WO | 05105404 A1 | 11/2005 |

\* cited by examiner

THERMOPLASTIC INJECTION MOLDED AND FLUSHABLE MATERIAL

BACKGROUND

The present disclosure relates generally to tampon applicators. Vaginal tampons are disposable absorbent articles sized and shaped (e.g., cylindrical) for insertion into a women's vaginal canal for absorption of body fluids generally discharged during the woman's menstrual period. Insertion of the tampon into the vaginal canal is commonly achieved using a tampon applicator that comes initially assembled with the tampon.

Tampon applicators are typically of a two-piece construction, including a barrel in which the tampon is initially housed and a plunger moveable telescopically relative to the barrel to push the tampon out of the barrel and into the vaginal canal. The barrel has a tip that generally retains the tampon within the barrel until pushed through the tip by the plunger. In normal use, the applicator and more particularly the barrel of the applicator is held by the user by gripping one portion of the barrel (e.g., toward the trailing or plunger end of the barrel) and inserting the barrel, tip end first, into the vaginal canal. The barrel is pushed partially into the canal so that a portion (e.g., toward the leading or exit end of the tampon barrel) is disposed within the vaginal canal and is contact with the walls lining the canal. The plunger is then used to push the tampon out through the tip of the barrel and into the canal. The plunger and barrel are then removed from the vaginal canal, leaving the tampon in place.

Flushable feminine care products provide consumers with discretion and convenience benefits. Current plastic tampon applicators, however, are made of injection molded materials such as polyolefins (e.g., polypropylenes or polyethylenes) and polyesters that are not biodegradable or renewable, as the use of biodegradable polymers in an injection molded part is problematic due to their high cost and to the difficulty involved with thermally processing such polymers. As a result, consumers must dispose of tampon applicators in a separate waste receptacle, which results in a challenge for consumers to dispose of the applicators in a discrete and convenient manner. Furthermore, the soiled or used tampon applicator can also pose a biohazard or potential health hazard. Although current plastic tampon applicators are not supposed to be flushed, some consumers can nevertheless attempt to flush the applicators in the toilet, which can lead to clogging of sewer pipes and municipal waste water treatment facilities. Attempts have been made to mold cold water-dispersible materials such as poly(vinyl alcohol) (PVOH) to alleviate these problems, but such attempts have not been successful. Instead, when using PVOH in tampon applicators, the materials must be solution processed so they can be formed into a tampon applicator that has a thick enough wall, and such solution processing is a slow, costly, environmentally-unsustainable process that necessitates high energy requirements. Further, although cardboard applicators have been developed, the cardboard must often be coated to decrease the coefficient of friction of the applicator to a comfortable level for consumers, and the coatings used are not environmentally friendly and add to the costs associated with forming the applicator.

Recent efforts on flushable applicators used a pin-dipping process and hydroxyl propyl methyl cellulose (HPMC) materials that were highly dispersible in cold water. The applicators, however, began dissolving during the insertion process and were extremely brittle and not amenable to current converting processes. Preliminary work produced a blend of HPMC and a proprietary resin that is also dispersible in cold water and shown the capability to be injection molded. The large amount of plasticizer used in these early formulations, however, proved to be an issue during long term storage.

As such, a need currently exists for a thermoplastic, water-dispersible composition that can be injection molded, where such compositions can be successfully formed into a tampon applicator. A need also exists for a water-dispersible applicator that is comfortable to insert and that does not begin to break down upon insertion or during storage.

SUMMARY

In one aspect, a water-dispersible injection-moldable composition includes partially-hydrolyzed polyvinyl alcohol (PVOH), polyethylene glycol (PEG), plasticizer, and a hydrophobic polymeric component, wherein the composition has a melt flow index of 5-180.

In an alternate aspect, a water-dispersible injection-moldable composition includes 55 wt. % to 75 wt. % partially-hydrolyzed polyvinyl alcohol (PVOH), 15 wt. % to 25 wt. % polyethylene glycol (PEG), 9 wt. % to 14 wt. % plasticizer, and 3 wt. % to 4 wt. % hydrophobic polymeric component.

In another aspect, a water-dispersible injection-moldable composition includes 55 wt. % to 75 wt. % partially-hydrolyzed polyvinyl alcohol (PVOH), 15 wt. % to 25 wt. % polyethylene glycol (PEG), 9 wt. % to 14 wt. % glycerin, and 0.5 wt. % to 4 wt. % polyethylene.

Objects and advantages of the disclosure are set forth below in the following description, or can be learned through practice of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
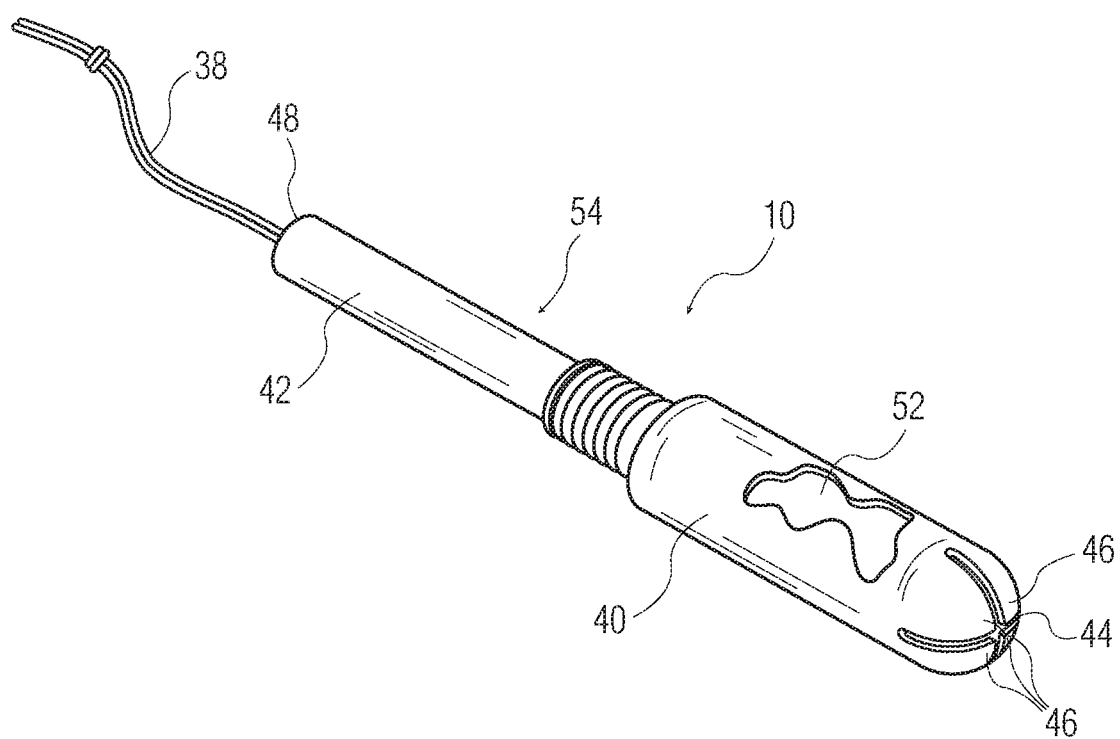
FIG. 1 is a perspective view of one aspect of a water-dispersible tampon applicator as contemplated by the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Generally speaking, the present disclosure is directed to a thermoplastic composition that is water-sensitive (e.g., water-soluble, water-dispersible, etc.) in that it loses its integrity over time in the presence of water, yet also has a high enough melt flow index and a low enough melt viscosity such that it can be molded into an article such as a tampon applicator. For instance, the thermoplastic composition described herein has a high enough melt flow index and a low enough melt viscosity such that it can be injected molded. The composition contains partially-hydrolyzed PVOH, polyethylene glycol (PEG), a plasticizer, and a hydrophobic polymeric component such as polyethylene. The desired water-sensitive attributes and mechanical properties of the composition and the resulting molded articles, such as tampon applicators, can be achieved in the present disclosure by selectively controlling a variety of aspects of the composition, including the nature of each of the components employed, the relative amount of each component, the ratio of the weight percentage of one component to the weight percentage of another component, and the manner in which the composition is formed.

The central aspect of the disclosure is that a tampon applicator barrel is sufficiently water dispersible (passes slosh box test), yet its properties are not significantly deteriorated before and during tampon insertion (passes insertion force test). If a tampon applicator begins to disperse too much during insertion, the barrel begins to stick and the insertion force increases too much. The present disclosure prevents this by delaying or significantly slowing water dispersion during tampon applicator insertion. This delay is linked to the surface morphology of the barrel and the presence of a hydrophobic polymer such as polyethylene (PE) at the surface.

This surface is created by fast cooling of the barrel in the mold of a uniform anhydrous ternary thermoplastic blend of PVOH, PEG, and small amount of PE to a temperature below the Upper Critical Solution Temperature (UCST) of the blend. During molding, when the temperature falls below the blend UCST, the PE migrates to the surface with the PEG. During this migration the PE migrates initially earlier and faster than the PEG to the surface, but later the PEG begins to displace the PE at the surface. The PEG does not begin to migrate until the blend temperature is below the UCST. Fast cooling freezes the surface morphology into a metastable state with enough PE at the surface to adequately delay dispersion. Too much PE would make a barrel that will not have adequate dispersibility. Enough plasticizer glycerin is added to allow fast compounding and high speed injection molding. The present disclosure makes a metastable polymer into a stable polymeric structured product, or at least stable for a period long enough for the tampon applicator to be used.

Additional information with respect to the morphology of the present disclosure and the potential for stabilization by specific interactions between components can be found with respect to hydrophobic interactions between the PVOH and PE at www.google.com/?gws_rd=ssl#q=Ultra-thin+films+on+polyvinyl+alcohol+on+hydrophobic+surfaces, and with respect to hydrophilic/hydrogen bonding interactions between PVOH, PEG, and glycerin at www.meplab.fudan.edu.cn/infonet/assays/1999/27.pdf, both of which are incorporated herein by reference to the extent they do not conflict herewith. Further information can be found at www.google.com/url?sa=t&rct=j&q=&esrc=s&source=web&cd=1&cad=rja&uact=8&ved=0ahUKEwi-utWwlurPAhUq-0oMKHTKaD5QQFggcMAA&url=https%3A%2F%2Fwww.physics.ncsu.edu%2Fstxm%2Fpubs%2FMacroMatEng00_274-1.pdf&usg=AFQjCNHrrc_Fput_ZYD-RKbmTaR8ttMZrwQ&bvm=bv.136499718,d.amc, and in Kolahchi et al., "Surface morphology and properties of ternary polymer blends: effect of the migration of minor components," J. Phys. Chem. B 2014, 118, 6316-6323, both of which are incorporated herein by reference to the extent they do not conflict herewith.

I. APPLICATOR DESIGN

As illustrated in the tampon assembly 10 of FIG. 1, the tampon applicator 54 comprises an outer tube 40 and an inner tube 42. The outer tube 40 is sized and shaped to house a tampon 52. A portion of the outer tube 40 is partially broken away in FIG. 1 to illustrate the tampon 52. In the illustrated aspect, the outer tube 40 has a substantially smooth exterior surface, which facilitates insertion of the tampon applicator 54 without subjecting the internal tissues to abrasion. The outer tube 40 may be coated to give it a high slip characteristic. The illustrated outer tube 40 is a straight, elongated cylindrical tube. It is understood however that the applicator 54 could have different shapes and sizes than those illustrated and described herein.

Extending outwardly from the outer tube is an insertion tip 44. The insertion tip 44, which is formed as one-piece with the outer tube 40, may be dome-shaped to facilitate insertion of the outer tube into a woman's vagina in a comfortable manner. The illustrated insertion tip 44 is made of a thin, flexible material and has a plurality of soft, flexible petals 46 that are arranged to form the dome-shape. The petals 46 are capable of radially flexing (i.e., bending outward) to provide an enlarged opening through which the tampon 52 can exit when it is pushed forward by the inner tube 42. It is to be understood, however, that the outer tube 40 may be formed without the insertion tip 44. Without the insertion tip, the outer tube includes an opened end (not shown) through which the tampon 52 can exit when it is pushed forward by the inner tube.

The inner tube 42 is an elongate cylinder that is used to engage the tampon 52 contained in the outer tube 40. A free end 48 of the inner tube 42 is configured so that the user can move the inner tube with respect to the outer tube 40. In other words, the free end 48 functions as a grip for the forefinger of the user. The inner tube 42 is used to push the tampon 52 out of the outer tube 40 and into the woman's vagina by telescopically moving into the outer tube. As the inner tube 42 is pushed into the outer tube 40 by the user, the tampon 52 is forced forward against the insertion tip 44. The contact by the tampon 52 causes the petals 46 of the insertion tip 44 to radially open to a diameter sufficient to allow the tampon to exit the outer tube 40 and into the woman's vagina. With the tampon 52 properly positioned in the woman's vagina, the tampon applicator 54 is withdrawn. In a used configuration of the tampon applicator 54, the inner tube 42 is received in the outer tube 40.

The inner tube 42, the outer tube 40, and the insertion tip 44 can be formed from one or more layers, where one layer includes the water-dispersible, thermoplastic composition of the present invention. Further, to prevent the applicator 54 from prematurely disintegrating due to moisture during use and/or to reduce the coefficient of friction of the applicator 54 to make it more comfortable for the user, it can be coated with a water-insoluble material that also has a low coefficient of friction to enhance comfort and prevent disintegration during insertion of the applicator 54. The structure of the tampon applicator described above is conventional and known to those skilled in the art, and is described, for instance, in U.S. Pat. No. 8,317,765 to Loyd, et al., which is incorporated herein in its entirety by reference thereto for all purposes. Other tampon applicator structures that can be formed from the thermoplastic composition of the present invention are described, for instance, in U.S. Pat. No. 4,921,474 to Suzuki, et al. and U.S. Pat. No. 5,389,068 to Keck, as well as U.S. Patent Application Publication Nos. 2010/0016780 to VanDenBogart, et al. and 2012/0204410 to Matalish, et al., which are incorporated herein in their entirety by reference thereto for all purposes.

Generally speaking, frictional forces occur between any two contacting bodies where there are forces tending to slide one of the bodies relative to the other. The frictional forces act parallel to the contacting surfaces and opposite the forces tending to cause sliding between the bodies. Further, the frictional forces are proportional to normal forces on the bodies and to the tendency of the bodies to grip each other.

As used herein, the coefficient of friction is the ratio of the frictional force between the bodies to the normal force between the bodies. The coefficient of friction is different between bodies at rest and bodies moving relative to each other. In general, two bodies contacting one another, but not moving relative to one another, will exhibit greater frictional resistance to motion than bodies that are moving relative to one another. Hence, a static coefficient of friction (i.e., a coefficient of friction between bodies that are not moving relative to each other) can but need not necessarily be somewhat greater than a dynamic coefficient of friction (i.e., a coefficient of friction between bodies that are moving relative to each other). Larger coefficients of friction correspond to larger amounts of friction between bodies, while smaller frictional coefficients correspond to smaller amounts of friction. As used further herein, the term coefficient of friction refers to at least one of a static coefficient friction and a dynamic coefficient of friction. In particularly suitable aspects, the coefficient of friction differential described previously is present for both static and dynamic coefficients of friction.

One or more additives can be added to the polymeric first layer 81 of the barrel 23 (prior to molding) to enhance the slip characteristic (e.g., to provide a low coefficient of friction) of the barrel outer surface at least at the central region 43 of the barrel and more suitably at the central region and tip region 45 of the barrel. For example, suitable such additives include without limitation erucamide, dimethicone, oleamide, fatty acid amide and combinations thereof. It is understood that other additives can used to provide enhanced slip characteristics to the barrel 23 outer surface without departing from the scope of this disclosure. In other aspects the barrel 23 can instead, or additionally, be coated with a friction reducing, or slip agent such as, without limitation, wax, polyethylene, silicone, cellophane, clay and combinations thereof. In still other suitable aspects the barrel 23 can include a polymer blend melted together and co-extruded to provide a low coefficient of friction.

In the illustrated aspect, the barrel 23 is further constructed so that the barrel outer surface at the tip region 45 has a lower coefficient of friction than at the central region 43 of the barrel to facilitate easier insertion of the barrel, inner end first, into the vaginal canal. This is particularly useful on days that a period is relatively light. For example, the outer surface of the barrel 23 at the tip region 45 can be configured to have a substantially lower surface roughness than at the central region 43 of the barrel, and more suitably the tip region can be substantially smooth or polished to reduce the coefficient of friction of the tip region relative to that of the central region. As a particular example, the surface roughness (that provides a tactile perception to the user) of the central region 43 of the barrel can have a surface roughness of less than or equal to about 36 and is more suitably about 27 in accordance with VDI Richtlinie [Standard] 3400. VDI Richtlinie 3400 has the German title: "Electroerosive Bearbeitung, Begriffe, Verfahren, Anwendung" [Electrical Discharge Machining, Definitions, Process, Application], published by the Verein Deutscher Ingenieure [Association of German Engineers] in June 1975.

In other aspects, the tip region 45 of the barrel 23 can instead, or additionally be coated with a friction reducing agent so that the outer surface of the barrel at the tip region has a lower coefficient of friction than that of the central region of the barrel. Providing a surface roughness differential between the tip region 45 and the central region 43 also serves as a visual indicator of the reduced friction coefficient at the tip region.

II. APPLICATOR MATERIALS

As described above, a water-dispersible injection-moldable resin for use in a flushable tampon applicator of the structure described herein is needed. All previous attempts to make a flushable injection molded tampon applicator have failed because the material could not be injection molded at low cycle times, and because the applicators were difficult to insert under moist conditions or had poor shelf-lives under high-moisture conditions. This disclosure allows for the successful production of a flushable tampon applicator that provides consumers a clean experience by eliminating the messiness of applicator disposal.

PVOH is a water-soluble, repulpable, and biodegradable resin with excellent aroma and oxygen barrier properties and resistance to most organic solvents. The polymer is used extensively in adhesives, textile sizing, and paper coating. Despite its excellent mechanical, physical, and chemical properties, the end uses of PVOH have been limited to those uses in which it is supplied as a solution in water. This limitation is partly due to the fact that vinyl alcohol polymers in an unplasticized state have a high degree of crystallinity and show little to no thermoplasticity before the occurrence of decomposition that starts at about 170° C. and becomes pronounced at 200° C., which is well below its crystalline melting point.

Attempts have been made to use PVOH in injecting molding for disposable sanitary products such as tampon applicators. These can yield molded parts that are stiff when removed from the molding machine but pick up moisture from the atmosphere and become too flexible for machine handling in the manufacture of tampon applicators. Other attempts use complex mixtures of materials, multiple types of PVOH, and/or various coatings. Tampon applicators made primarily from PVOH are water-dispersible and biodegradable; however, such applicators have been shown to suffer from issues involving moisture sensitivity, stability, odor, and stickiness. Hence there have been no commercially successful launches of these applicators.

Other attempts in addressing the flushability of plastic tampon applicators include plastic applicators made from other water-soluble materials such as polyethylene oxide polymers, thermoplastic starch, and hydroxypropyl cellulose; plastic tampon applicators made from combinations of water-soluble and water-insoluble/biodegradable materials such as combinations of PVOH and polycaprolactone, combinations of polyethylene oxide and polycaprolactone, combinations of polyethylene oxide and polyolefins such as polypropylene and polyethylene; and combinations of PVOH and polyethylene oxide polymers. Again, none of these attempts to produce a truly flushable product have seen commercial application.

A water-dispersible injection-moldable resin based on PVOH has been developed for use as the primary resin for injection molding outer and inner (plunger) tubes in current tampon applicators. The resin is a blend of single low molecular weight partially-hydrolyzed PVOH, a plasticizer such as glycerin, a high molecular weight polyethylene glycol (PEG), and a hydrophobic polymer component such as polyethylene. In addition, the applicator resin formulation can include other materials such as color additives, antioxidants, surface finish, and release agents/lubricants such as a euricamide release agent.

A single grade of PVOH, specifically a PVOH partially hydrolyzed at 87-89%, with a low molecular weight provides the speed of dispersibility required for flushability. This PVOH is plasticized with glycerin to adjust the melt flow rate to be compatible with injection molding. The level of plasticizer is low enough that it does not bloom during storage, which would result in an unusable product. The plasticizer level also contributes to the softness or hardness of the final product. A high molecular weight polyethylene glycol is added to reduce wet coefficient of friction.

A. Polyvinyl Alcohol Polymer

The water-dispersible, thermoplastic composition includes one or more polymers containing a repeating unit having a functional hydroxyl group, such as polyvinyl alcohol ("PVOH") and copolymers of polyvinyl alcohol (e.g., ethylene vinyl alcohol copolymers, methyl methacrylate vinyl alcohol copolymers, etc.). Vinyl alcohol polymers, for instance, have at least two or more vinyl alcohol units in the molecule and can be a homopolymer of vinyl alcohol or a copolymer containing other monomer units. Vinyl alcohol homopolymers can be obtained by hydrolysis of a vinyl ester polymer, such as vinyl formate, vinyl acetate, or vinyl propionate. Vinyl alcohol copolymers can be obtained by hydrolysis of a copolymer of a vinyl ester with an olefin having 2 to 30 carbon atoms, such as ethylene, propylene, or 1-butene; an unsaturated carboxylic acid having 3 to 30 carbon atoms, such as acrylic acid, methacrylic acid, crotonic acid, maleic acid, or fumaric acid or an ester, salt, anhydride or amide thereof; an unsaturated nitrile having 3 to 30 carbon atoms, such as acrylonitrile or methacrylonitrile; a vinyl ether having 3 to 30 carbon atoms, such as methyl vinyl ether or ethyl vinyl ether; and so forth. The degree of hydrolysis can be selected to optimize solubility, for example, of the polymer. For example, the degree of hydrolysis can be from about 60 mole % to about 95 mole %, in some aspects from about 80 mole % to about 90 mole %, in some aspects from about 85 mole % to about 89 mole %, and in some aspects from about 87 mole % to about 89 mole %. These partially-hydrolyzed polyvinyl alcohols are cold-water soluble. In contrast, completely-hydrolyzed or nearly-hydrolyzed polyvinyl alcohols are not soluble in cold water.

Examples of suitable partially-hydrolyzed polyvinyl alcohol polymers are available under the designations SELVOL 203, 205, 502, 504, 508, 513, 518, 523, 530, or 540 PVOH from Sekisui Specialty Chemicals America, LLC of Dallas, Tex. For instance, SELVOL 203 PVOH has a percent hydrolysis of 87% to 89% and a viscosity of 3.5 to 4.5 centipoise (cps) as determined from a 4% solids aqueous solution at 20° C. SELVOL 205 PVOH has a percent hydrolysis of 87% to 89% and a viscosity of 5.2 to 6.2 cps as determined using a 4% solids aqueous solution at 20° C. SELVOL 502 PVOH has a percent hydrolysis of 87% to 89% and a viscosity of 3.0 to 3.7 cps as determined using a 4% solids aqueous solution at 20° C. SELVOL 504 PVOH has a percent hydrolysis of 87% to 89% and a viscosity of 4.0 to 5.0 cps as determined from a 4% solids aqueous solution at 20° C. SELVOL 508 PVOH has a percent hydrolysis of 87% to 89% and a viscosity of 7.0 to 10.0 cps as determined as determined from a 4% solids aqueous solution at 20° C. Other suitable partially-hydrolyzed polyvinyl alcohol polymers are available under the designations ELVANOL 50-14, 50-26, 50-42, 51-03, 51-04, 51-05, 51-08, and 52-22 PVOH from DuPont. For instance, ELVANOL 51-05 PVOH has a percent hydrolysis of 87% to 89% and a viscosity of 5.0 to 6.0 cps as determined from a 4% solids aqueous solution at 20° C.

In the present disclosure, the polyvinyl alcohols characterized as having a low viscosity include SELVOL 502 PVOH (3.0 to 3.7 cps), where the midpoint or average viscosity for low-viscosity polyvinyl alcohol is generally less than about 3.35 cps, as determined by averaging the minimum and maximum viscosities provided for commercially available partially-hydrolyzed polyvinyl alcohols. The polyvinyl alcohols characterized as having a high viscosity include SELVOL 203 PVOH (3.5 to 4.5 cps), SELVOL 504 PVOH (4.0-5.0 cps), ELVANOL 51-05 PVOH (5.0 to 6.0 cps), SELVOL 205 PVOH (5.2 to 6.2 cps), and SELVOL 508 PVOH (7.0-10.0 cps), where the midpoint or average viscosity for the high-viscosity polyvinyl alcohol polymers is at least about 4.0 cps, as determined by averaging the minimum and maximum viscosities provided for commercially-available partially-hydrolyzed polyvinyl alcohols.

B. Polyethylene Glycol

Polyethylene glycol (PEG) having average molecular weights of between about 300 and 2,000,000, alternatively, between about 500 and 2,000,000, alternatively between about 1000 and 1,000,000, alternatively between about 1000 and 400,000, alternatively, between about 1000 and 100,000, alternatively between about 3000 and 100,000 are desirable for use in the present disclosure. In another aspect, PEGs having average molecular weights between about 3000 and 35,000 are desirable. As the ethylene oxide chain impacts functionality of the invention, PEG variants with different functional groups on each end will also be acceptable for use in the invention. Linear as well as branched forms will likewise be acceptable for use in the invention. In a further aspect, PEGs having average molecular weights of between about 4000 and 12000 are desirable. In another aspect, PEGs having average molecular weights of about 8000 are desirable. Such PEG materials are available, for example, from the Dow Chemical Company under the trade name CARBOWAX.

C. Plasticizer

A plasticizer is also employed in the water-dispersible thermoplastic composition to help render the water-soluble polymer thermoplastic and thus suitable for extrusion into pellets and subsequent injection molding. Suitable plasticizers include, for instance, polyhydric alcohol plasticizers such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), and polyethylene glycols. Also suitable are hydrogen-bond-forming organic compounds that do not have a hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers can include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids can also be used, such as ethylene acrylic acid, ethylene maleic acid, butadiene acrylic acid, butadiene maleic acid, propylene acrylic acid, propylene maleic acid, and other hydrocarbon-based acids. A low molecular weight plasticizer is preferred, such as less than about 20,000 g/mol, preferably less than about 5,000 g/mol, and more preferably less than about 1,000 g/mol.

The plasticizer can be incorporated into the composition of the present disclosure using any of a variety of known techniques. For example, water-soluble polymers can be "pre-plasticized" prior to incorporation into the composition. Alternatively, one or more of the components can be plasticized at the same time they are blended together. Batch and/or continuous melt blending techniques can be employed to blend the components. For example, a mixer/kneader, Banbury mixer, Farrel continuous mixer, single-screw extruder, twin-screw extruder, roll mill, etc. can be used. One particularly suitable melt-blending device is a co-rotating, twin-screw extruder (e.g., USALAB twin-screw extruder available from Thermo Electron Corporation of Stone, England or an extruder available from Werner-Pfleiderer from Ramsey, N.J.). Such extruders can include feeding and venting ports and provide high intensity distributive and dispersive mixing. For example, the water-soluble polymer can be initially fed to a feeding port of the twin-screw extruder to form a composition. Thereafter, a plasticizer can be injected into the composition. Alternatively, the composition can be simultaneously fed to the feed throat of the extruder or separately at a different point along the length of the extruder. Melt blending can occur at any of a variety of temperatures, such as from about 30° C. to about 240° C., in some aspects, from about 40° C. to about 200° C., and in other aspects, from about 50° C. to about 180° C.

Plasticizers can be present in the water-dispersible, thermoplastic composition in an amount ranging from about 2 wt. % to about 50 wt. %, such as from about 3 wt. % to about 45 wt. %, and such as from about 5 wt. % to about 40 wt. %, based on the total weight of the composition. In some aspects, the plasticizer can be present in an amount of 10 wt. % or greater, such as from about 10 wt. % to about 35 wt. %, such as from about 10 wt. % to about 30 wt. %, and such as from about 10 wt. % to about 25 wt. % based on the total weight of the composition.

D. Hydrophobic Polymeric Component

It appears that a small amount of a hydrophobic polymer added to the blend enhances the performance of the tampon applicator. The hydrophobic polymer can be added to the blend on its own, or as a component in another addition, such as in a coloring agent. Hydrophobic polymers include polyethylene.

It is believed that during molding, when the temperature falls below the blend UCST, the hydrophobic polymer such as PE migrates to the surface with the PEG. During this migration the PE migrates initially earlier and faster than the PEG to the surface, but later the PEG begins to displace the PE at the surface. The PEG does not begin to migrate until the blend temperature is below the UCST. Fast cooling freezes the surface morphology into a metastable state with enough PE at the surface to adequately delay dispersion. Too much PE, however, would make a tampon applicator barrel that will not have adequate dispersibility.

E. Coloring Agents

In addition, the water-dispersible, thermoplastic composition can contain one or more coloring agents (e.g., pigment or dye). Typically, a pigment refers to a colorant based on inorganic or organic particles that do not dissolve in water or solvents. Usually pigments form an emulsion or a suspension in water. On the other hand, a dye generally refers to a colorant that is soluble in water or solvents.

The pigment or dye can be present in an amount effective to be visible once the composition is formed into an injection molded article so that articles formed from the composition can have an aesthetically-pleasing appearance to the user. Suitable organic pigments include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860:1), toluidine red (for example, Pigment Red 22 CI No. 12315), dioxazine violet (for example, Pigment Violet 23 CI No, 51319), phthalocyanine green (for example, Pigment Green 7 CI No. 74260), phthalocyanine blue (for example, Pigment Blue 15 CI No. 74160), and naphthoic acid red (for example, Pigment Red 48:2 CI No. 15865:2). Inorganic pigments include titanium dioxide (for example, Pigment White 6 CI No. 77891), iron oxides (for example, red, yellow, and brown), chromium oxide (for example, green), and ferric ammonium ferrocyanide (for example, blue).

Suitable dyes that can be used include, for instance, acid dyes and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes, and the like.

When present, the coloring agents can be present in the water-dispersible thermoplastic composition in an amount ranging from about 0.5 wt. % to about 20 wt. %, such as from about 1 wt. % to about 15 wt. %, such as from about 1.5 wt. % to about 12.5 wt %, and such as from about 2 wt. % to about 10 wt. % based on the total weight of the water-dispersible thermoplastic composition.

F. Other Optional Components

In addition to the components noted above, other additives can also be incorporated into the composition of the present disclosure, such as dispersion aids, melt stabilizers, processing stabilizers, heat stabilizers, light stabilizers, antioxidants, heat aging stabilizers, whitening agents, antiblocking agents, bonding agents, and lubricants. Dispersion aids, for instance, can also be employed to help create a uniform dispersion of the PVOH/plasticizer mixture and retard or prevent separation into constituent phases. Likewise, the dispersion aids can also improve the water dispersibility of the composition. Although any dispersion aid can generally be employed in the present disclosure, surfactants having a certain hydrophilic/lipophilic balance ("HLB") can improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some aspects of the present disclosure, the HLB value of the surfactants is from about 1 to about 20, from about 1 to about 15, or from about 2 to about 10. If desired, two or more surfactants can be employed that have HLB values either below or above the desired value, but together have an average HLB value within the desired range.

One particularly suitable class of surfactants for use in the present disclosure is that of nonionic surfactants, which typically have a hydrophobic base (e.g., a long chain alkyl group or an alkylated aryl group) and a hydrophilic chain (e.g., chain containing ethoxy and/or propoxy moieties). For instance, some suitable nonionic surfactants that can be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular aspect, the nonionic surfactant can be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters can be saturated or unsaturated, substituted or unsubstituted, and can contain from 6 to 22 carbon atoms, from 8 to 18 carbon atoms, or from 12 to 14 carbon atoms. In one particular aspect, mono- and di-glycerides of fatty acids can be employed in the present disclosure.

When employed, the dispersion aid(s) typically constitute from about 0.01 wt. % to about 15 wt. %, from about 0.1 wt. % to about 10 wt. %, from about 0.5 wt. % to about 5 wt. %, and from about 1 wt. % to about 3 wt. % based on the total weight of the water-dispersible thermoplastic composition.

III. APPLICATOR STABILITY/WRAPPER

Flushable articles need to be protected from moisture because an article that will disperse in water is prone to degradation in humidity or other moisture. An article wrapper material with a WVTR rating of at most 0.05 g/100 in$^2$/day is generally required.

IV. OPTIMIZING CONDITIONS

The base resin of choice for a flushable applicator is Selvol 502, a partially-hydrolyzed PVOH with a viscosity range of 3.0-3.7 cps and 35-40% crystalline and an average molecular weight of 20,000 daltons. Glycerin plasticizes the PVOH and softens the resultant applicator tubes with an optimum content around 11-13%, resulting in a melt flow of 90 g/10 min for the compounded resin. The addition of high molecular weight PEG (e.g., PEG 8000) reduces the wet insertion force of PVOH applicators to that of current polyethylene applicators.

This base resin provides a thermoformable PVOH composition that can be melt extruded or injection molded into a thin wall structure which is flushable and biodegradable while retaining its wall integrity and stiffness at high humidity.

PEG may be uniformly dispersed in the PVOH; while in the solid state, the PEG molecules do not inhabit intact crystallites, and plasticization occurs in the amorphous region only, during crystallization, the PEG species are eliminated from the PVOH lattice. The PEG species in the PVOH matrix may form hydrogen bonds with the PVOH segments. When crystallization occurs, such PEG species should be removed from the PVOH crystallites, as a result, the crystallization would be delayed. The more the PEG species that are incorporated, the slower would be the crystallization.

In one aspect, a specific formulation meets physical properties and user needs such as insertion and removal force and pledget expulsion force. This formulation includes a blend of 55 wt. % to 75 wt. % lower molecular weight partially-hydrolyzed PVOH, 15 wt. % to 25 wt. % higher molecular weight PEG, 9 wt. % to 14 wt. % glycerin, 3 wt. % to 4 wt. % colorant within an ethylene matrix, <1 wt. % colorant package additives including one or more of the following processing, stabilization, and finishing adjuncts: antioxidants, finishing additive, release agents, and processing lubricants The low molecular weight PVOH is highly dispersible, breaking down in a modified slosh box test in 30-40 minutes. Its melt flow rate is easily modified to allow for injection molding with only small amounts of plasticizer (9 wt. % to 13 wt. %) that eliminates the greasy feel associated with surface migration of glycerin when incorporated at the higher levels used for higher molecular weight PVOH resins or mixtures of PVOH resins.

The processes described herein using PVOH/PEG/glycerin/PE work best in the range of 40° C. to 200° C. The operation temperature of the extruder will be between the liquid-liquid separation temperature of the PVOH/PEG/glycerin blend and the melting temperatures of PVOH & PEG in the blend, and the decomposition temperature of the PVOH/PEG/glycerin blend. At a temperature above the liquid-liquid separation temperature the blend is miscible and below it the blend is immiscible. The approximate separation temperature will be between approximately 55° C. and 60° C. A literature value (US2003/0156618) for the PVOH/PEG UCST is around 42° C. A literature value (SELVOL 205 PVOH trade literature) for the glass transition temperature of "pure" PVOH is around 58° C.; the value found herein was between 50° C. and 75° C. A literature value (CARBOWAX PEG 8000 PEG, Dow technical data sheet) for the melting point of PEG 8000 is between 55° C. and 62° C.; the value found herein was around 65° C. The blend value for the melting point of PEG found herein is around 59° C. and the blend value for the glass transition of PVOH appears to be around 25° C. The literature value for the melting point of pure glycerin is around 18° C. The approximate decomposition temperature is between 170° C. and 200° C. The literature value for rapid thermal decomposition of glycerin indicates that pure glycerin begins to decompose around 177° C. and ends around 231° C. The literature value for rapid thermal decomposition of PVOH is between 200° C. and 500° C.; the value found herein is over 200° C. The literature value for the rapid thermal decomposition of PEG is over 300° C.; the value found herein is over 320° C.

It appears a certain amount of PE or any other hydrophobic and immiscible polymer needs to be included in the PVOH/PEG/glycerin/PE blend. The composition described herein includes a small amount of a hydrophobic and immiscible polymer within the blend. The literature (U.S. Pat. No. 6,544,661) indicates that the amount of PE will need be below 20% to allow some dispersibility; the work described herein suggests a more preferred amount of less than 5%.

Described herein is the process of making PVOH compositions where the necessary energy is added to melt the PVOH and additional energy is added to shear the areas of PVOH crystallinity in the melt, while at the same time removing the shearing energy to prevent the melt temperature from exceeding the PVOH decomposition temperature. The extruder requires intensive mixing elements to provide the requisite shearing energy. The shearing energy generated in a particular zone of the extruder should not be greater than that which can be removed by cooling, otherwise decomposition results. The process provides sufficient mixing of the PVOH/PEG species and rapid cooling of the melt to reduce the final crystallinity and maintain the interaction of PVOH and PEG species. The PEG acts as a spacer to enlarge the distance among PVOH segments. The spacing effect decreases the glass transition temperature of PVOH and along with the presence of glycerin, results in plasticization.

Injection moldable formulations of PVOH and PEG were developed through compounding on a Coperion ZSK30 co-rotating twin screw extruder. The process involves first melting and mixing the PVOH and PEG, plasticizing the PVOH with glycerin, de-volatizing of moisture from the melt, followed by rapidly cooling of the melt with air prior to pelletization of the cooled strands.

The Coperion ZSK30 has seven heated zones over thirteen barrel sections. Resin pellets can be feed into the main feeding zone using any of the three feeders. The melt process is initiated in the second barrel section followed by the injection of the liquid plasticizer. The melt is intensively mixed prior to the addition of filler or additive, when applicable, in barrel seven. Further mixing is applied to the melt before moisture and volatiles are vented in barrel twelve. The melt is pressurized and extruded through a three-hole strand die. A typical temperature profile using a screw speed of 160 rpm is shown in Table 1.

TABLE 1

PVOH Compounding Temperature Profile

| HZ-1 (° C.) | HZ-2 (° C.) | HZ-3 (° C.) | HZ-4 (° C.) | HZ-5 (° C.) | HZ-6 (° C.) | Die (° C.) |
|---|---|---|---|---|---|---|
| 90 | 130 | 165 | 195 | 190 | 180 | 160 |

The resulting strands were well mixed without evidence of gels or crystals with a moisture content of 0.5-0.8%. The strands were cooled with room temperature air (22° C.) air, using only 6 of a possible 13 fans (500 fpm/fan) along the cooling belt, moving at 18' per minute, prior to being pelletized. The resulting pellets have a diameter of 0.12 inches and a height of 0.13 inches. The retention time for the PVOH in the extruder was between 1.25 and 3.75 minutes.

Effect of temperature and screw speed was studied using three temperature profiles and three screw speeds (160, 300, 500 rpm), as shown in Table 2.

TABLE 2

Compounding Optimization Temperature Profiles

| | HZ-1 (° C.) | HZ-2 (° C.) | HZ-3 (° C.) | HZ-4 (° C.) | HZ-5 (° C.) | HZ-6 (° C.) | Die (° C.) |
|---|---|---|---|---|---|---|---|
| Ultra Low | 90 | 130 | 130 | 130 | 130 | 130 | 150 |
| Low Temp | 90 | 140 | 150 | 150 | 150 | 150 | 150 |
| High Temp | 90 | 130 | 165 | 195 | 190 | 180 | 160 |

The PVOH raw material as received from the vendor contains between 2-3% moisture. To consistently remove this moisture during compounding to less than 1%, the melt must be raised above 150° C. This remaining moisture acts as a plasticizer and therefore raises the melt flow from 60 g/10 min to 80 g/10 min.

The optimum conditions, where the specific energy required is lowest, is at the higher temperature and lowest screw speed. These optimum conditions also produce the best material physical properties.

Coefficient of friction and dispersibility were not affected by the conditions of compounding as was expected.

A method of compounding has been optimized for screw design, screw speed, and temperature profile on a co-rotating twin screw extruder to produce a compounded formulated resin that has removed the PVOH crystallinity, completely dispersed the PVOH and PEG components, reduced moisture, and removed heat from the PVOH during compounding to minimize degradation. By quickly air cooling the polymer strands, the PVOH/PEG blend was maintained and re-crystallization of the PVOH domains was not allowed.

With respect to the specific situation of an injection-molded tampon applicator, a user-friendly, successful flushable tampon applicator is accomplished by the creation of a unique morphology within the plastic applicator. Compounding has created a blend of PVOH and PEG in which the polymer chains are equally dispersed with each other. Quick cooling freezes this morphology in the outer thicknesses of the plastic part. Maintaining the mixture of PVOH and PEG allows the applicator to be inserted under moist conditions with the equivalent force of a standard polyethylene applicator. This solves what has always been the drawback of PVOH applicators and more specifically single grade PVOH applicators.

PVOH is typically considered to be an adhesive under wet conditions, and PEG can be used as an adhesion amplifier. The unexpected result of combining PVOH and PEG was the production of a material with reduced tackiness, even under wet conditions. Without being limited to by theory, it appears that the PVOH and the PEG, both being porous-structure-forming, become interspersed, each essentially occupying the pores of the other. This interspersion pushes the small amount of polyethylene available in the colorant package or added on its own to the surface where it forms a very thin skin. This skin protects the water-dispersible components of the formulation from moisture long enough to prevent the water-dispersible components from becoming tacky, thus reducing the wet insertion force of the applicator.

Reference now will be made in detail to various aspects of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one aspect, can be used on another aspect to yield a still further aspect. Thus, it is intended that the present disclosure covers such modifications and variations as come within the scope of the appended claims and their equivalents.

V. EXAMPLES

A. Test Methods

Melt Flow Rate: The melt flow rate ("MFR") is the weight of a polymer (in grams) forced through an extrusion rheometer orifice (0.0825-inch diameter) when subjected to a load of 2160 grams in 10 minutes, typically at 190° C. or 230°. Unless otherwise indicated, melt flow rate is measured in accordance with ASTM Test Method D1239 with a Tinius Olsen Extrusion Plastometer. It should be noted that the melt flow rate measured at 190° C. can be referred to as the melt flow index (MFI), while those measured at other temperatures are called melt flow rates (MFR).

Tensile Properties: Tensile properties were determined by following ASTM D638-10 guidelines. ASTM D638-10 Type V injection-molded test specimens were pulled via a MTS Mold 810 tensile frame with a 3,300 pound load cell. Five specimens were pulled from each example. The average values for peak stress (tensile strength), elongation at break, and modulus were reported. The maximum elongation that could be determined was 127% based on the tensile frame used, and the elongation was actually higher in the samples having 127% elongation readings.

Flushability Assessment: Disintegration testing was performed as outlined in Guidance Document for Assessing the Flushability of Nonwoven Consumer Products (INDA and EDANA, 2006); Test FG 522.2 Tier 2—Slosh Box Disintegration Test. A round disc of each test resin is weighed and placed in 2L of water maintained at 15° C. and agitated at 25-26 cycles per minute. The time for the material to disperse completely and pass through a 1 mm screen is recorded. After a maximum of 180 minutes, the test is stopped, any remaining pieces larger than 1 mm are collected, dried, and weighed. The percent weight remaining of the disc is recorded.

B. Materials 1. 65.5% lower molecular weight partially-hydrolyzed polyvinyl alcohol (SELVOL 502 PVOH produced by Sekisui, Dallas, Tex.)
2. 20% higher molecular weight polyethylene glycol (CARBOWAX PEG 8000 produced by Dow Chemical, Houston, Tex.)
3. 11% glycerin (EMERY COGNIS 916 from Cognis Corporation, Cincinnati, Ohio)
4. 3.5% colorant within an ethylene matrix (SCC 85283 from Standridge Color Corp., Social Circle, Ga.)
5. any one or more of the following processing, stabilization, and finishing adjuncts: antioxidants, finishing additive, release agents, and processing lubricants (these are all part of the colorant package, <1%).

C. Process

Resin Compounding: In general, formulated resins were produced using a Coperion ZSK30 (30 mm diameter/1340 mm processing length compounding screw) co-rotating twin screw extruder with 7 heated sections and a resin-compounding screw design. Resins were produced at a rate of 20 pounds per hour. PVOH and PVOH blends were dry blended prior to feeding through the main feed section. The color/slip agent was fed using a separate feeder, also into the main feed section. Glycerin was injected in section 3 and calcium carbonate was fed into section 4. The temperature profile per section, beginning at the main feed section was 90°, 130°, 160°, 190°, 190°, 180°, and 145° C. The melt pressure ranged between 30-50 psi with the extruder torque of between 35 to 45%. The extruded polymer was uniform in color and flowed well from the die. The strands were air cooled and pelletized.

Figure 2:
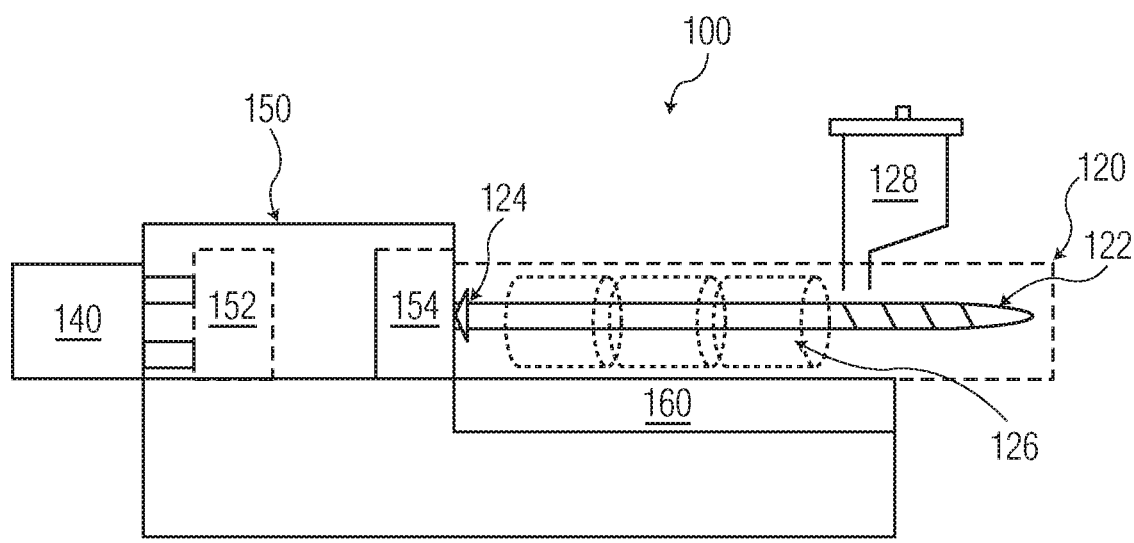
FIG. 2 is a schematic view of a representative injection molding apparatus used to manufacture the tampon applicator of FIG. 1.

Injection Molding: The examples where processed on a Boy Machine 22D Injection Molder. This model has a 24.2 ton clamping force unit, a 24 mm plasticizing unit, and a shot size of 34 grams. FIG. 2 is a schematic of a basic injection molding machine 100. It shows the main components: the injection unit 120, the clamping unit 140, and the control panel 160. The injection molding cycle begins when the mold 150 closes, pairing the moveable platen 152 with the fixed platen 154. At this point, the screw 122 moves forward and injects the material through the nozzle 124 into the sprue, and the material fills the mold 150 (runners, gates, and cavities). During the packing phase, additional material is packed into the cavities. The material is cooled and solidifies in the mold while the screw 122 rotates counterclockwise backward, melting the plastic for the next shot using heating bands 126. New material is supplied by the hopper 128. The mold 150 opens and the parts are ejected. The next cycle begins when the mold 150 closes again.

Figure 3:
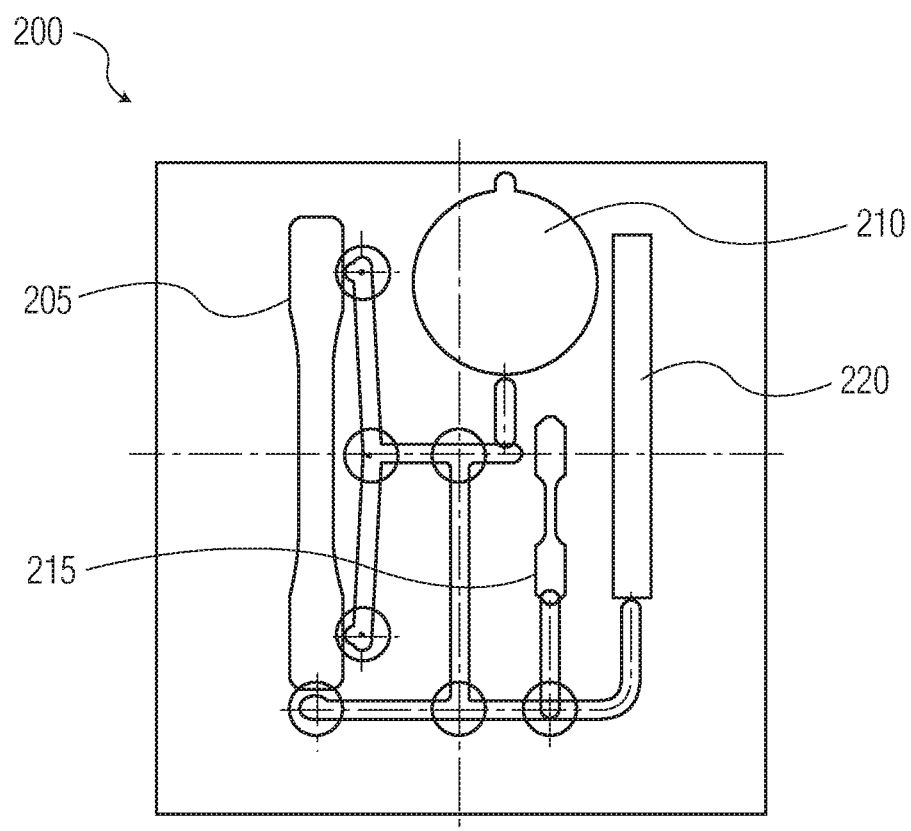
FIG. 3 is a schematic plan view of a standard test sample mold used in the present application.

The mold 200 used to produce specimens was an ASTM D638 standard test specimen mold from Master Precision Products, Inc., as illustrated in FIG. 3. This mold 200 contains a Tensile Type I specimen 205, a round disk 210, a Tensile Type V specimen 215, and an Izod bar 220.

Injection-molded applicators were produced at Schoettli Group Industie Grossholz, 8253 Diessenhofen, Switzerland using a pilot mold for both barrels and plungers.

A process to blend the above composition with a co-rotating twin screw extruder includes the steps:

1. Add solid components (PVOH, PEG, colorant) at a mass rate (lbs/hr) different for each solid (feed rate based as percentage of total output)
2. Add liquid components at a mass rate lbs/hr (based as percentage of total output)
3. Mix solids and liquids at an extruder speed of 160 rpm
4. Melt solid components at an extruder temperature between 170° C. and 195° C.
5. Extrude strands of blend at melt temperature between 175° C. and 180° C.
6. Quench strands with room temperature air (22° C.) air, using 6 of a possible 13 fans (500 fpm/fan) along the cooling belt, moving at 18 feet per minute
7. Pelletize strands into pellets with a diameter of 0.12 inches and a height of 0.13 inches
8. Resonate time of the compounding process is between 1.25 and 3.75 minutes and the energy input rate of the compounding process is between 0.04 and 0.05 J/lb.

An injection molding process for the blend described above includes the steps:

1. Pump a blend with a temperature between 175° C. and 180° C. into parts mold with a surface temperature less than 10° C.
2. The mold has a blend-compatible permanent release coating (tungsten disulfide)
3. Keep in mold until blend solidify or vitrify or for a time between t1-t2 (seconds)
4. Eject the part from mold and cool the part with cool dry air.

D. Results

Both polyethylene (control applicators) and PVOH/PEG tubes from this trial were tested for insertion force. PVOH/PEG tubes had lower insertion force than PVOH alone. The PVOH/PEG applicators were equivalent to control applicators.

In a first particular aspect, a water-dispersible injection-moldable composition includes partially-hydrolyzed polyvinyl alcohol (PVOH), polyethylene glycol (PEG), plasticizer, and a hydrophobic polymeric component, wherein the composition has a melt flow index of 5-180.

A second particular aspect includes the first particular aspect, wherein the hydrophobic polymeric component is a colorant within an ethylene matrix.

A third particular aspect includes the first and/or second aspect, wherein the hydrophobic polymeric component is polyethylene.

A fourth particular aspect includes one or more of aspects 1-3, wherein the composition has a melt flow index of 60-90.

A fifth particular aspect includes one or more of aspects 1-4, wherein the composition includes 55 wt. % to 75 wt. % partially-hydrolyzed PVOH.

A sixth particular aspect includes one or more of aspects 1-5, wherein the composition includes 15 wt. % to 25 wt. % PEG.

A seventh particular aspect includes one or more of aspects 1-6, wherein the composition includes 9 wt. % to 14 wt. % plasticizer.

An eighth particular aspect includes one or more of aspects 1-7, wherein the plasticizer is glycerin.

A ninth particular aspect includes one or more of aspects 1-8, wherein the PVOH has a viscosity range of 3.0-3.7 cps.

A tenth particular aspect includes one or more of aspects 1-9, wherein the PVOH has a hydrolysis of 87% to 89%.

An eleventh particular aspect includes one or more of aspects 1-10, wherein the composition is flushable according to Guidance Document for Assessing the Flushability of Nonwoven Consumer Products (INDA and EDANA, 2006); Test FG 522.2 Tier 2—Slosh Box Disintegration Test.

In a twelfth particular aspect, a water-dispersible injection-moldable composition includes 55 wt. % to 75 wt. % partially-hydrolyzed polyvinyl alcohol (PVOH), 15 wt. % to 25 wt. % polyethylene glycol (PEG), 9 wt. % to 14 wt. % plasticizer, and 3 wt. % to 4 wt. % hydrophobic polymeric component.

A thirteenth particular aspect includes the twelfth particular aspect, wherein the composition has a melt flow index of 5-180.

A fourteenth particular aspect includes the twelfth aspect and/or the thirteenth aspect, wherein the composition has a melt flow index of 60-90.

A fifteenth particular aspect includes one or more of aspects 12-14, wherein the hydrophobic polymeric component is a colorant within an ethylene matrix.

A sixteenth particular aspect includes one or more of aspects 12-15, wherein the hydrophobic polymeric component is polyethylene.

A seventeenth particular aspect includes one or more of aspects 12-16, wherein the PVOH has a hydrolysis of 87% to 89%.

In an eighteenth particular aspect, a water-dispersible injection-moldable composition includes 55 wt. % to 75 wt. % partially-hydrolyzed polyvinyl alcohol (PVOH), 15 wt. % to 25 wt. % polyethylene glycol (PEG), 9 wt. % to 14 wt. % glycerin, and 0.5 wt. % to 4 wt. % polyethylene.

A nineteenth particular aspect includes the eighteenth particular aspect, wherein the PVOH has a hydrolysis of 87% to 89%.

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there can be additional elements other than the listed elements.

As various changes could be made in the above products without departing from the scope of the disclosure, it is intended that all matter contained in the above description and shown in the accompanying drawings shall be interpreted as illustrative and not in a limiting sense.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. A water-dispersible injection-moldable composition comprising:
    partially-hydrolyzed polyvinyl alcohol (PVOH);
    polyethylene glycol (PEG);
    plasticizer; and
    a hydrophobic polymeric component, wherein the composition has a melt flow index of 5-180.
2. The composition of claim 1, wherein the hydrophobic polymeric component is a colorant within an ethylene matrix.
3. The composition of claim 1, wherein the hydrophobic polymeric component is polyethylene.
4. The composition of claim 1, wherein the composition has a melt flow index of 60-90.
5. The composition of claim 1, wherein the composition includes 55 wt. % to 75 wt. % partially-hydrolyzed PVOH.
6. The composition of claim 1, wherein the composition includes 15 wt. % to 25 wt. % PEG.
7. The composition of claim 1, wherein the composition includes 9 wt. % to 14 wt. % plasticizer.
8. The composition of claim 1, wherein the plasticizer is glycerin.
9. The composition of claim 1, wherein the PVOH has a viscosity range of 3.0-3.7 cps.
10. The composition of claim 1, wherein the PVOH has a hydrolysis of 87% to 89%.
11. A water-dispersible injection-moldable composition comprising:
    55 wt. % to 75 wt. % partially-hydrolyzed polyvinyl alcohol (PVOH);
    15 wt. % to 25 wt. % polyethylene glycol (PEG);
    9 wt. % to 14 wt. % glycerin; and
    0.5 wt. % to 4 wt. % polyethylene.
12. The composition of claim 11, wherein the PVOH has a hydrolysis of 87% to 89%.

* * * * *